United States Patent [19]
Prentice et al.

[11] Patent Number: 6,119,854
[45] Date of Patent: Sep. 19, 2000

[54] SANITARY TOOTHBRUSH STORAGE UNIT

[76] Inventors: Thomas Prentice; Paulette Prentice, both of 2740 Grubb Rd., Wilmington, Del. 19810

[21] Appl. No.: 09/482,721

[22] Filed: Jan. 13, 2000

[51] Int. Cl.[7] ............................. B65D 81/24; B65D 85/20
[52] U.S. Cl. ................................ 206/209.1; 206/362.1
[58] Field of Search ......................... 206/209, 209.1, 206/210, 361, 362, 362.1, 362.2, 581, 823

[56] References Cited

U.S. PATENT DOCUMENTS

| | | |
|---|---|---|
| 942,058 | 12/1909 | De Gowin . |
| 1,050,864 | 1/1913 | Smith . |
| 1,070,858 | 11/1913 | Trayne . |
| 1,079,618 | 11/1913 | Trayne . |
| 1,424,434 | 8/1922 | Ausbel . |
| 1,588,781 | 6/1926 | Stoddard . |
| 1,713,379 | 5/1929 | Fronwiler . |
| 2,012,685 | 8/1935 | Dosea .................................. 206/209.1 |
| 3,867,096 | 2/1975 | Doucette . |
| 4,214,657 | 7/1980 | Winston ............................... 206/209.1 |
| 4,473,152 | 9/1984 | Jump et al. ........................... 206/209.1 |
| 4,585,119 | 4/1986 | Boyington ............................ 206/209.1 |
| 4,625,119 | 11/1986 | Murdock . |
| 4,740,706 | 4/1988 | Murdock . |
| 4,759,383 | 7/1988 | Phillips ................................ 206/209.1 |
| 4,915,219 | 4/1990 | Ohimo . |
| 5,086,916 | 2/1992 | Gray ..................................... 206/209.1 |
| 5,377,824 | 1/1995 | Seymour . |
| 5,690,214 | 11/1997 | Gaines et al. ........................ 206/209.1 |
| 5,725,091 | 3/1998 | Knoebel ............................... 206/209.1 |

*Primary Examiner*—Jacob K. Ackun
*Attorney, Agent, or Firm*—Ratner & Prestia

[57] ABSTRACT

A sanitary storage unit for storage of one or more toothbrushes, each toothbrush having a handle end and a bristle end, the sanitary storage unit comprising an upper chamber, at least one removable reservoir supported under the upper chamber and adapted to hold a liquid, a middle divider mounted between the reservoir and the upper chamber, and a cover adapted for opening and closing the upper chamber. The middle divider has at least one hole therein adapted for insertion of a toothbrush therethrough such that the bristle end of the toothbrush rests in the reservoir and the handle end of the toothbrush extends through the hole into the upper chamber. The cover may be attached to the storage unit at a hinge about which the cover can pivot open and closed. The reservoir may be slidably removable from the storage unit on a track or on a shelf. The reservoir is preferably filled with a sanitizing liquid and may include one or more dividers that divide the reservoir into a plurality of separate compartments, or may comprise a plurality of reservoirs attached together with the fluid in each reservoir isolated from all other reservoirs. The number of reservoirs or reservoir compartments is preferably the same as the number of holes in the middle divider.

29 Claims, 2 Drawing Sheets

U.S. Patent    Sep. 19, 2000    Sheet 1 of 2    6,119,854
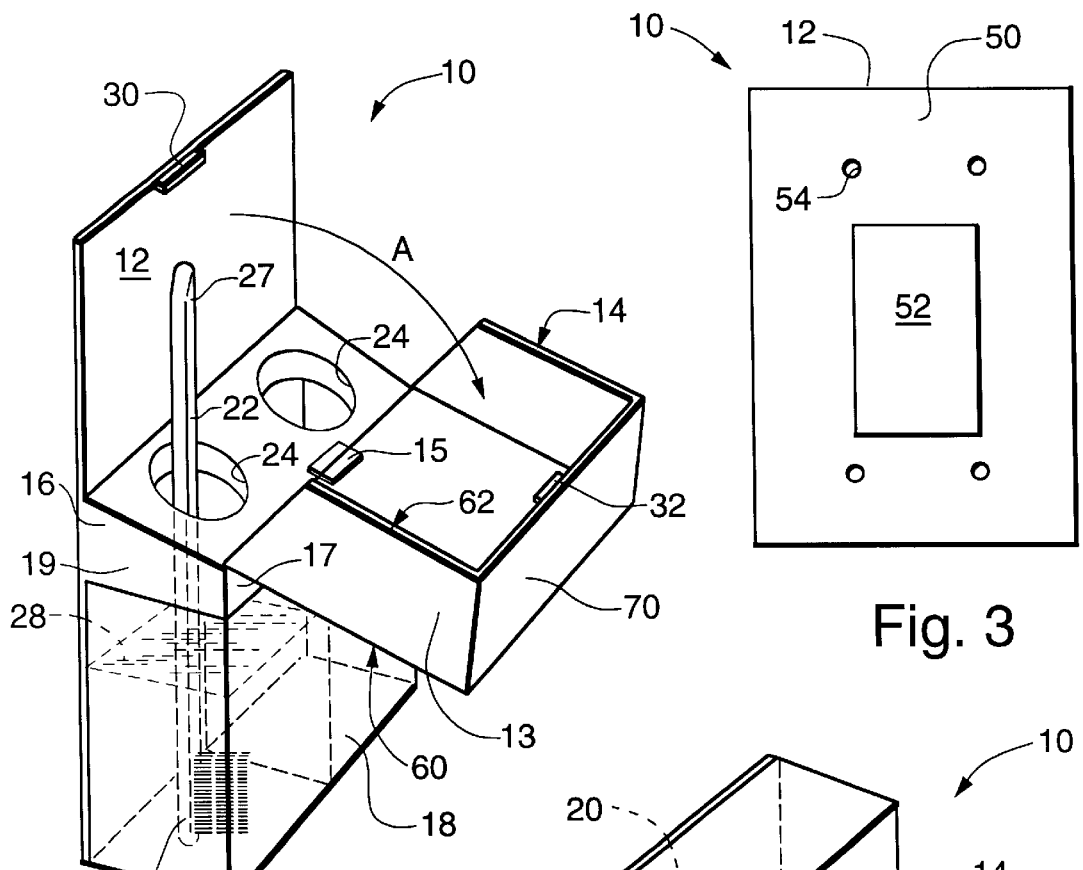
Fig. 1
Fig. 3
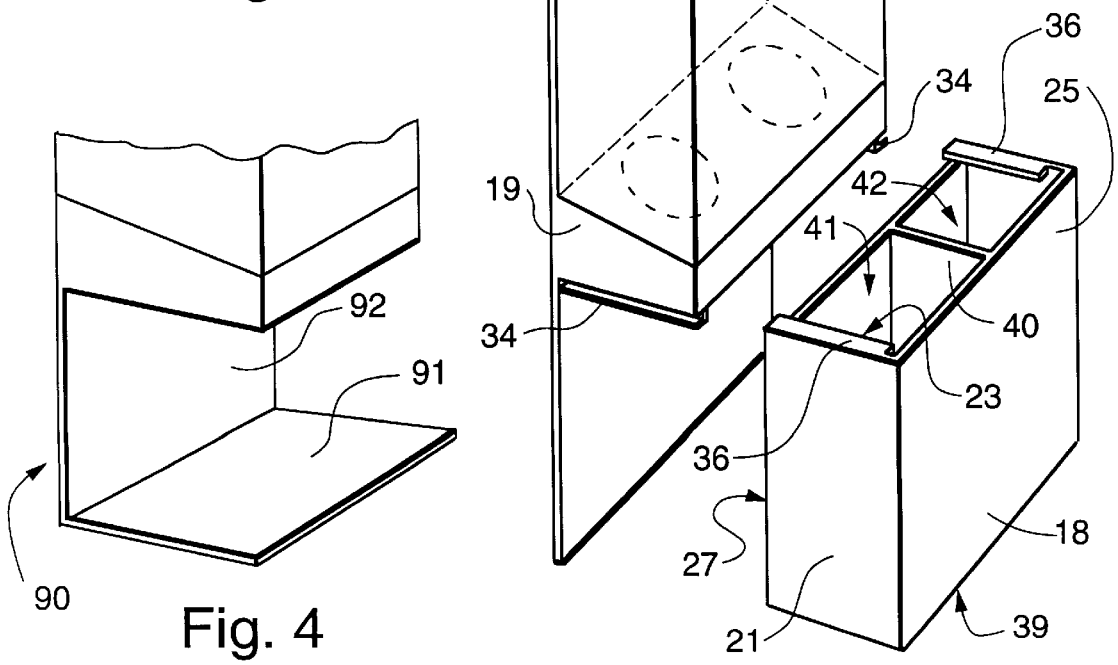
Fig. 4
Fig. 2

SANITARY TOOTHBRUSH STORAGE UNIT

TECHNICAL FIELD

The present invention relates generally to a storage unit for toothbrushes and, more specifically, to a sanitary storage unit for storing toothbrushes with the bristle end of the toothbrush immersed in a sanitary liquid.

BACKGROUND OF THE INVENTION

Toothbrushes are commonly stored in any number of ways, many of which are unsightly and/or unsanitary. Often, toothbrushes are stored uncovered on countertops, in drawers, or in unsanitized holders where they are exposed to germs and contaminants in the air. Toothbrushes stored on the countertop, whether in or out of a particular toothbrush holder, may leave toothpaste residue on the countertop or on the holder and in general, toothbrushes stored in this manner may lead to a cluttered countertop appearance.

The general problem of unsanitary toothbrush storage has been recognized by many in the past, who have devised any number of toothbrush holders designed to sanitize the toothbrushes by immersing the bristles in a sanitizing liquid, exposing them to ultraviolet light, or exposing them to a sanitizing gas. Many such devices are complicated or bulky and, for example, do not allow for easy replenishment of the sanitizing liquid or washing of the reservoir for the sanitizing liquid. Others are merely adapted to sit on the countertop, thus still adding to general countertop clutter.

It is an object of the present invention, therefore, to provide a sanitary toothbrush storage unit that allows for storage of toothbrushes in sanitary liquid while furthermore providing simple access to the liquid reservoir for replenishment or exchange of the sanitizing liquid and for cleaning out the reservoir. It is a further optional object of the invention to provide a sanitary toothbrush storage unit that reduces countertop clutter and is aesthetically pleasing.

SUMMARY OF THE INVENTION

The present invention provides a sanitary storage unit for storage of one or more toothbrushes, each toothbrush having a handle end and a bristle end, the sanitary storage unit comprising an upper chamber, at least one removable reservoir adapted to hold a liquid and supported underneath the upper chamber, a middle divider mounted between the reservoir and the upper chamber, and a cover adapted for opening and closing the upper chamber. The middle divider has at least one hole therein adapted for insertion of a toothbrush therethrough such that the bristle end of the toothbrush rests in the reservoir and the handle end of the toothbrush extends through the hole into the upper chamber.

The cover may be attached to the storage unit at a hinge about which the cover can pivot open and closed. The back wall of the storage unit may be adapted for mounting upon a flat vertical surface, such as a bathroom wall, such as with a double-sided adhesive or screws.

The reservoir may be slidably removable from the storage unit. The middle divider may comprise a first member of a track depending therefrom and the reservoir may comprise a second member of the track, the second member and the first member adapted to slide relative to one another from a fully engaged configuration to a fully disengaged configuration. The track in the fully engaged configuration is adapted to support the weight of the reservoir when filled with liquid to a predetermined level. Instead of or in addition to the track, the sanitary storage unit may comprise a bottom shelf perpendicular to the back wall, and the reservoir may be adapted to rest on the bottom shelf.

The reservoir is preferably filled with a sanitizing liquid such as mouthwash, antiseptic liquid, germicidal liquid, antibacterial liquid, a solution of dilute hypochlorite, a solution of dilute hydrogen peroxide, or a combination thereof. The reservoir, the middle divider, and the lid may comprise opaque materials for hiding the contents therein, such as plastic for lowest cost, or such as wood, brass, stainless steel, marble, granite, or a decorative resin, to maximize the aesthetic appearance.

The reservoir may include one or more dividers that divide the reservoir into a plurality of separate compartments, or may comprise a plurality of reservoirs attached together with the fluid in each reservoir isolated from all other reservoirs. The number of reservoirs or reservoir compartments is preferably the same as the number of holes in the middle divider.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1 is a perspective view of an embodiment of the present invention showing the hidden insider of the reservoir in dashed lines.

FIG. 2 is a perspective view of the embodiment shown in FIG. 1, showing the reservoir fully disengaged from the rest of the holder and showing a track for sliding the reservoir into and out of position.

FIG. 3 is a view of the rear side of a back panel of an exemplary embodiment of the present invention.

FIG. 4 is a partial view of an alternative embodiment showing a bottom shelf for holding the reservoir.

DETAILED DESCRIPTION OF INVENTION

Figure 5:
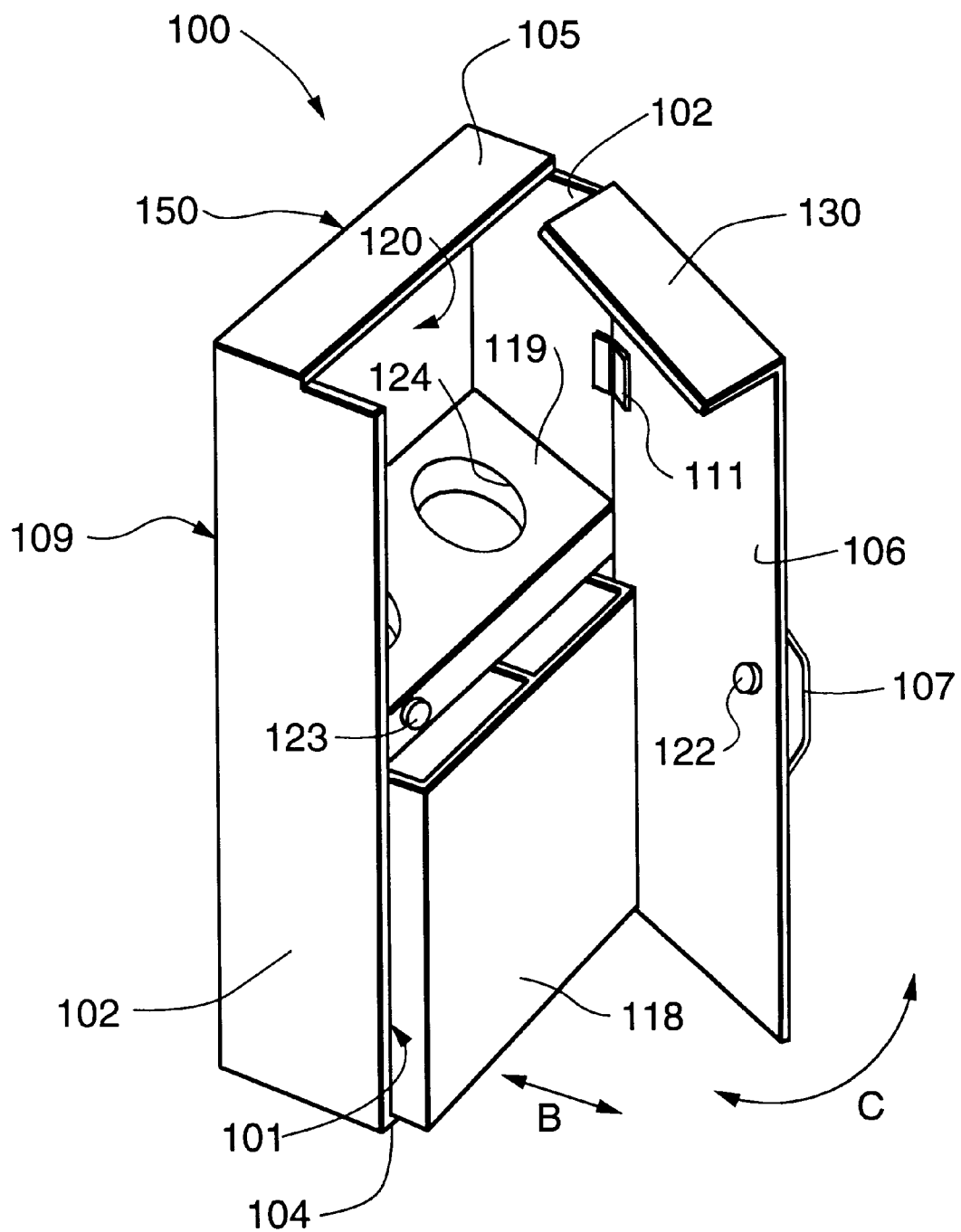
FIG. 5 is a perspective view of an alternative embodiment comprising a cabinet with a single door, shown with the door open and the reservoir partially retracted from the lower chamber.

Referring now to the drawing, wherein like reference numerals refer to like elements throughout, FIGS. 1–3 depict an exemplary embodiment of a sanitary toothbrush storage unit 10 of the present invention. As shown in FIG. 1, sanitary toothbrush storage unit 10 comprises a back panel 12, a lid 14, a middle divider 16, and a reservoir 18. Lid or cover 14 is attached to middle divider 16 by hinge 15, and is pivotable between the open position shown in FIG. 1 and the closed position shown in FIG. 2. As shown in FIG. 2, when lid 14 is in a closed position, the walls of the lid, middle divider 16, and back panel 12 define an upper chamber 20. A toothbrush 22 can be inserted through one of the holes 24 in middle divider 16 such that bristle end 26 of the toothbrush rests in reservoir 18 submerged in a sanitizing liquid 28, and handle end 27 of the toothbrush extends through hole 24 into upper chamber 20.

As shown in FIG. 2, middle divider 16 comprises a first set of track elements 34 and reservoir 18 comprises a second set of track elements 36. The first and second track elements 34 and 36 are adapted to slide relative to one another so that reservoir 18 can slide into a fully engaged position as shown in FIG. 1 and a fully disengaged position shown in FIG. 2. As shown in FIG. 2, first track element 34 is in the nature of a groove depending from sidewalls 19 of middle divider 16 and second track element 36 is in the nature of a rail that fits within the groove and is mounted to top edge 23 of sidewalls 21 of reservoir 18. Of course, the first track element 34 may be the rail and the second track element 36 the groove, or both elements may comprise different components of any type of track known in the art. Although shown in FIGS. 1 and 2 with a single reservoir unit 18 having two compartments 41 and 42, unit 10 may comprise separable reservoirs that each have their own track elements on either side. Furthermore, although shown in FIGS. 1 and 2 with the track elements mating at top edge 23 of sidewalls 21 of reservoir 18 to allow the reservoir to slide in and out from front to back, the track elements may be located at the top edge of front wall 25 and back wall 27 of reservoir 18 such that it can be inserted from side to side. In an alternative embodiment, sidewalls 19 of middle divider 16 may extend downward further such that the track elements on the middle divider engage mating track elements mounted to sidewalls 21 (or front wall 25 and back wall 27) of reservoir 18 on an intermediate plane between top edge 23 and bottom edge 29 of the reservoir.

Referring now to FIG. 4, in an alternative embodiment, the reservoir (not shown) may merely slide into and out of position under holes (not shown in FIG. 4) on a shelf 91 that projects from back wall 92 of sanitary toothbrush holder 90. Such a shelf may have one or more recessed areas, not shown, provided to align with the bottom of the reservoir or reservoirs to assure proper placement of the reservoir(s). A single reservoir or divided reservoir unit, or individual reservoirs may be used with such a shelf. If individual reservoirs are used with a shelf, however, it is desirable for the design to have some means for preventing the individual reservoirs from moving or tipping over once placed. Rather than support the entire weight of the liquid-filled reservoir(s) by the track, and to assure that the reservoirs are secured once placed, it may be desirable to have both shelf 91 and track elements 34 and 36 such that the reservoir is supported to some degree by both.

As shown in FIG. 1, back panel 12 may comprise a first interlocking closure element 30 and lid 14 may comprise a second interlocking closure element 32. Thus, when lid 14 is closed, the first and second interlocking closure elements 30 and 32 snap together and the lid cannot fall open without some manipulation by the user. As shown in FIG. 1, the interlocking closure elements are merely plastic tabs that snap together with one another, such as are well-known in the art, but the interlocking closure elements can comprise any interlocking elements known in the art. The location of the interlocking closure elements are not limited to the locations shown in FIG. 1, but can be located such that they align with one another anywhere on the perimeter of the lid.

Hinge 15 as shown in FIGS. 1 and 2 is attached to front wall 17 of middle template 16 and opens downward in the direction of arrow A and closes in the direction opposite arrow A. Hinge 15 may be located elsewhere than where shown in FIG. 1, however, such that the lid opens upward or to either side. More than one hinge may be present. Preferably, the interlocking closure elements are located opposite the hinge or hinges. In an alternative embodiment, the lid may be balanced such that no closure elements are needed. In yet another embodiment, the lid may not be attached at all, and may be freely removable. For easy one handed operation, however, the lid is preferably attached as shown in FIG. 1.

First and second interlocking closure elements (not shown), similar to those shown with respect to lid 14, may be located on reservoir 18 and on a corresponding portion of back panel 12 or middle divider 16 such that the reservoir may be held firmly in the fully engaged position until some intentional manipulation by the user.

Reservoir 18 may comprise a single liquid reservoir, or preferably may be divided into separate compartments by a divider 40. Divider 40 may comprise a removable divider that merely separates a single reservoir into separate compartments 41 and 42 with some or no liquid interaction between compartments. Alternatively, as shown in FIG. 2, divider 40 may be an integral wall such that compartments 41 and 42 are effectively two separate reservoirs attached together with the liquid in each reservoir isolated from the liquid in the other. As referred to herein, therefore, "divider" refers to any type of discrete divider that separates one section of a reservoir from another section or an integral wall between two separate reservoirs that are attached together as a single unit. Similarly, the term "reservoir" as used herein may refer to a single reservoir that is divided into separate compartments, to each of the separate compartments so divided, or to individual reservoirs attached together to form a multiple-reservoir unit such as reservoir 18 in FIG. 2.

Referring now to FIG. 3, there is shown a rear side 50 of back panel 12 (the front side is visible in FIG. 1). As discussed in the background section above, it may be desirable to remove the toothbrushes and any clutter associated therewith, from the countertop. Thus, toothbrush storage unit 10 is adapted for mounting on a flat vertical surface, such as a bathroom wall. Storage unit 10 may be mounted in any way known in the art, such as for example by double-sided adhesive 52 one side of which adheres to unit 10 and the other side of which adheres to a wall. The double-sided adhesive may extend only to one or more portions of rear 50 of back panel 12, or may extend across the entire surface area of the back panel rear. The double-sided tape may be provided to the consumer already stuck to unit 10 as shown in FIG. 3, or the user may have the choice of applying it if needed. Other adhesives, such as can be applied from simple tubes of adhesive may also be used for affixing storage unit 10 to the wall.

In the alternative or in addition, back panel 12 may comprise one or more screw holes 54 as shown in FIG. 3 (screw holes not shown in FIG. 1). Screw holes 54 are adapted to allow a threaded end of a screw (not shown) to pass therethrough but to retain the head end of the screw such that the unit can be secured to the wall with screws. The unit may come prepackaged with both the adhesive and the screws so that a consumer may choose the desired method for hanging. Preferably, screw holes 54, if any, are located such that reservoir 18 and lid 14 hide the screws when unit 10 is in a fully assembled and closed configuration (reservoir 18 fully engaged and lid 14 closed). It may be further desirable, however, to add covers or other decorative elements to hide the screws. In another alternative embodiment, back panel 12 may comprise a first component of an interlocking bracket (not shown) wherein the second component of the bracket is attached to the wall such that the entire unit may be hung upon and removed from the brackets.

Although sanitary toothbrush storage unit 10 may be adapted for mounting to the wall in a preferred embodiment, the storage unit can also sit directly on a countertop if the consumer desires. The preferred embodiment for such a countertop application is the embodiment shown in FIG. 4, such that when the reservoir (not shown) is removed, the unit can still stand freely on bottom shelf 91.

One advantage of sanitary toothbrush storage unit 10 over storage units known in the art, is that it is relatively simple and compact. For example, two toothbrushes can be stored in a storage unit that is 8 inches tall, 3 inches wide from side to side, and 1¾ inches deep from front to back. For such an 8×3×1¾ unit configured as shown in FIGS. 1 and 2, the reservoir may be 3½ inches tall and divided into two 1½ inch wide compartments. As can be seen in FIG. 1, sidewall 19 of middle divider 16 has a trapazoidal shape, the height of the trapezoid being taller in the back than in the front. In the exemplary embodiment of the size described above, the front height of the trapezoid (along front wall 17) may be ½ inch tall and the back height 1 inch tall. Accordingly, sidewalls 13 of lid 14 are also trapezoidal in shape with a front edge 60 having a height of 4 inches and a back edge 62 having a height of 3½ inches tall. Holes 24 may be oval in shape having a major diameter of 1¼ inches from front to back and a minor diameter of ¾ inches from side to side.

In addition to the advantageous compact size of the storage unit of this invention, reservoir 18 can be easily refilled merely by sliding it out and pouring liquid 28 into compartments 41 and 42. Furthermore, liquid 28 can occasionally be emptied entirely and the reservoir cleaned, such as by putting the reservoir in a dishwasher or manually washing it. To further maintain a desirable uncluttered look in the bathroom, storage unit 10 is preferably made of an opaque material to hide the contents inside, although if desired, the material may be translucent or transparent.

The simplicity of storage unit 10 means that all of the components can be made of low-cost materials such as plastic. In the alternative, however, it may be desirable to manufacture unit 10 from high-end decorative materials to match the countertop or cabinetry of the bathroom, such as wood, a decorative metal such as brass or stainless steel, a decorative stone such as marble or granite, or decorative resins such as Corian® methacrylate resin manufactured by DuPont of Wilmington, Del. The listed materials are merely examples, however, and are not intended to be limiting, as the unit may be manufactured of any material desired. Furthermore, novelty designs may be provided. For example for a children's bathroom, the design, rather than being substantially rectangular as shown in FIGS. 1–4, may resemble a favorite cartoon character, an animal, or some other item of interest to children. Similarly, the design may be provided with hardware and sculpting to match the bathroom cabinetry, or to be consistent with "country" decor, southwestern decor, art deco, or other interior design themes. If desired, the storage unit can be partially recessed into a wall in a like manner as a medicine cabinet. Such a recessed design, however, must provide adequate access for a user to completely place and retract the toothbrush.

Referring now to FIG. 5, in an alternative embodiment, particularly suited for a unit 100 made of a high-end decorative material such as those listed above, it may still be desirable for reservoir 118 to be made of plastic, but to further enclose the reservoir in a lower chamber 101 having sidewalls 102, a bottom 104, and a hinged door 106 that can be opened and closed. Sidewalls 102, a bottom 104, back 150, top 105 and hinged door 106 may all be made of the same high-end decorative materials in the manner of a cabinet 109. Reservoir 118 is removable along arrow B, as shown in FIG. 5 in a partially retracted position, and may be slideably removable on tracks as described above or merely may rest on cabinet bottom 104. Door 106 may have a handle or knob 107 and may have a first closure element 122, such as a piece of iron or steel, that is aligned with a second closure element 123, such as a magnet, mounted on the middle divider 119 or elsewhere on cabinet 109, so that the door may "stick" closed. The first and second closure elements may be any such elements commonly known in the art for keeping a door closed until a user performs an intentional act to open it. Unit 100 may include a single door 106, that opens and closes from the top, bottom, or either side (shown in FIG. 5 opened from the right side along arrow C) to enclose upper chamber 120, lower chamber 101, and middle divider 119 within cabinet 109 when closed, or may include multiple doors (not shown), one to open and close the upper chamber and another the open and close the lower chamber. Such a door 106 or doors (not shown) may be attached to cabinet 109 by one or more hinges 111.

Where cabinet 109 comprises high-end decorative materials, middle divider 119 may comprise plastic, for example if it is hidden with door 106 closed as in the configuration shown in FIG. 5, or may comprise high-end decorative materials also, especially in configurations having separate doors for the upper and lower chambers where at least a portion of the middle divider may be exposed. In the alternative, the exposed portions of a plastic middle divider may have a high-end material facade. Similarly, the configuration shown in FIG. 1 may comprise high-end materials for the cover 14 and any exposed portions of middle divider 19, and reservoir 18 may further comprise a facade of high-end materials on any exposed surfaces, thus providing an aesthetically pleasing appearance at potentially a lower cost.

As shown in FIG. 5, it may be preferable for the door to include a lid portion 130 that extends at least partially over upper chamber 120 and mates with top 105 such that the height of the upper chamber can be minimized while still allowing ample clearance for toothbrushes to be inserted and removed from holes 124. Although shown in FIG. 5 with a lid portion 130 that extends approximately half the depth of cabinet 109, the lid portion may extend to any depth as desired, including the entire depth of the cabinet to the extent that top 105 is shown in FIG. 5. Lid portion 130 may also be omitted entirely as long as the height of upper chamber 120 and the configuration of holes 124 is adequate to allow toothbrushes to be inserted and removed. Holes 124 may be configured such that toothbrushes may be inserted at an angle to allow a minimum height of upper chamber 120 and/or minimum depth of lid portion 130.

The cover for the upper enclosure may comprise a lid, as shown in FIGS. 1 and 2, that is attached to the middle divider or some other portion of the sanitizer, a door such as is shown in FIG. 4, or the cover may be an unattached, completely-removable element that can be taken on and off (not shown). As shown in FIG. 1, cover 14 may include a top wall 70 and side walls 13. Top 70, as discussed with respect to FIG. 5, may extend all the way to back panel 12 as shown in FIG. 1, or may extend to only a partial depth, similar to the configuration shown in FIG. 5. Similarly, side walls 13 may be split into a portion connected to back panel 12 and a portion connected to cover 14.

Although shown in FIGS. 1 and 2 with two holes 24 and two compartments 41 and 42 in reservoir 18, there may be any number of holes or compartments, including a single hole and reservoir. Preferably, the number of holes matches the number of compartments, each hole being aligned with one compartment.

Liquid 26 in reservoir 18 may be any suitable liquid known in the art. Mere water may be used, but preferably liquid 26 comprises a quantity of sanitizing liquid such as mouthwash, preferably an antiseptic mouthwash such as Listerine® marketed by the Warner-Lambert company of Morris Plains, N.J., or some other antiseptic, disinfectant, germicidal and/or antibacterial liquid approved for oral or dental use. Simple solutions of dilute hypochlorite or dilute hydrogen peroxide, concentrations of which acceptable for oral contact being well-known in the art, may also be suitable liquids.

Although the design of the reservoir is simple as illustrated herein, other modifications can be made as are known in the art. For example, the bottom of the reservoir may comprise a plurality of upwardly projecting fingers (not shown) such as are described in U.S. Pat. No. 5,107,987 to Palazzolo et al. to permit foreign material carried by the toothbrush to settle between the elements. Furthermore, some portion (not shown) of the holes in the middle divider or of another element (not shown) mounted in the reservoir may provide a necked-down section designed to flex the toothbrush bristles during entry and exit from the reservoir. Such a necked-down area, the concept of which is described generally in U.S. Pat. No. 4,585,119, for example, may provide mechanical action to release droplets of sanitizing liquid upon removal from the sanitizing liquid or may further remove foreign particles from the bristles upon placement into the sanitizing liquid.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A sanitary toothbrush storage unit for storage of one or more toothbrushes, each toothbrush having a handle end and a bristle end, the sanitary storage unit comprising:
   an upper chamber;
   at least one removable reservoir adapted to hold a liquid and supported below said upper chamber;
   a middle divider mounted between the reservoir and the upper chamber and having at least one hole therein adapted for insertion of a toothbrush therethrough such that the bristle end of the toothbrush rests in the reservoir and the handle end of the toothbrush extends through the hole into the upper chamber;
   a cover adapted for opening and closing the upper chamber.

2. The sanitary toothbrush storage unit of claim 1 wherein the cover is attached to the storage unit by a hinge about which the cover is adapted to pivot open and closed.

3. The sanitary toothbrush storage unit of claim 2 wherein an other end of the hinge is attached to the middle template.

4. The sanitary toothbrush storage unit of claim 3 wherein the storage unit has a front wall and a back wall and wherein the hinge is attached to the middle template at the front wall.

5. The sanitary toothbrush storage unit of claim 1 wherein the storage unit has a front wall and a back wall and the back wall is adapted to be mounted upon a flat vertical surface.

6. The sanitary toothbrush storage unit of claim 5 wherein the back wall includes a double-sided adhesive element adapted on one side to adhere to the sanitary storage unit and on an opposite side to adhere to the flat vertical surface.

7. The sanitary toothbrush storage unit of claim 5 wherein the back wall includes one or more mounting holes each adapted to pass a threaded end of a screw but to retain a head end of the screw such that the storage unit can be fastened to the flat vertical surface with one or more of said screws.

8. The sanitary toothbrush storage unit of claim 1 wherein the reservoir is slidably removable from the storage unit.

9. The sanitary toothbrush storage unit of claim 8 wherein the the middle divider comprises a first member of a track depending therefrom and the reservoir comprises a second member of said track, the second member and said first member adapted to slide relative to one another from a fully engaged configuration to a fully disengaged configuration.

10. The sanitary toothbrush storage unit of claim 9 wherein the reservoir has a predetermined weight when filled with said liquid to a predetermined level and in which said track in said fully engaged configuration is adapted to support all of or at least a portion of the weight of said reservoir when filled with said liquid to said predetermined level.

11. The sanitary toothbrush storage unit of claim 9 wherein the storage unit comprises a back wall and a first interlocking closure element and the reservoir comprises a second interlocking closure element, the first interlocking closure element and the second interlocking closure element adapted to interlock together when said reservoir is in the fully engaged configuration to prevent said reservoir from moving out of said fully engaged configuration without user manipulation.

12. The sanitary toothbrush storage unit of claim 1 wherein the storage unit comprises a back wall and a bottom shelf perpendicular to said back wall, in which said reservoir is adapted to rest upon said bottom shelf.

13. The sanitary toothbrush storage unit of claim 12 wherein the reservoir has a predetermined weight when filled with said liquid to a predetermined level and in which said bottom shelf is adapted to support all of or at least a portion of the weight of said reservoir when filled with said liquid to said predetermined level.

14. The sanitary toothbrush storage unit of claim 1 further comprising a liquid in said reservoir wherein said liquid is a sanitizing liquid selected from the group consisting of: mouthwash, antiseptic liquid, germicidal liquid, antibacterial liquid, disinfectant liquid, a solution of dilute hypochlorite, a solution of dilute hydrogen peroxide, or a combination thereof.

15. The sanitary toothbrush storage unit of claim 1 wherein said storage unit comprises a material from the group consisting of: plastic, wood, decorative metal, decorative stone, decorative resin, or a combination thereof.

16. The sanitary toothbrush storage unit of claim 1 wherein said reservoir, said middle divider, and said cover comprise opaque materials.

17. The sanitary toothbrush storage unit of claim 1 wherein the cover comprises a front wall, two opposite side walls, and a top wall.

18. The sanitary toothbrush storage unit of claim 1 where in the storage unit comprises a back wall and a first interlocking closure element and the cover comprises a second interlocking closure element, the first interlocking closure element and the second interlocking closure element adapted to interlock together when said cover is in a closed configuration to prevent said cover from moving to an open configuration without user manipulation.

19. The sanitary toothbrush storage unit of claim 1 wherein the reservoir includes one or more dividers that divide the reservoir into a plurality of separate compartments.

20. The sanitary toothbrush storage unit of claim 1 comprising a first plurality of reservoirs attached together, the fluid in each reservoir isolated from all other reservoirs.

21. The sanitary toothbrush storage unit of claim 1 comprising a first plurality of reservoirs or separate compartments within a single reservoir and comprising a second plurality of holes in said middle divider, the first plurality being equal to the second plurality.

22. The sanitary toothbrush storage unit of claim 21 comprising: two reservoirs or two separate compartments within a single reservoir, and two holes in said middle divider.

23. The sanitary toothbrush storage unit of claim 1 wherein the sanitary storage unit with the cover closed and the reservoir in a fully engaged position comprises a substantially rectangular box-like geometry.

24. The sanitary toothbrush storage unit of claim 1 wherein the sanitary storage unit comprises a cabinet further comprising a lower chamber in which the reservoir is disposed, and a cover for at least the lower chamber.

25. The sanitary toothbrush storage unit of claim 24 wherein the cover for the lower chamber and the cover for the upper chamber further comprise a single door extending across at least a front face of the cabinet.

26. The sanitary toothbrush storage unit of claim 25 wherein the door comprises a lid portion extending at least partially over the upper chamber.

27. A sanitary toothbrush storage unit for storage of one or more toothbrushes, each toothbrush having a handle end and a bristle end, the sanitary storage unit comprising:

a back wall adapted for mounting the sanitary storage unit upon a vertical flat surface;

an upper chamber;

a slideably-removable reservoir supported under said upper chamber and having a first plurality of compartments, each compartment adapted to hold a sanitizing liquid, the reservoir comprising a set of first track elements;

a middle divider mounted between the reservoir and the upper chamber and having a second plurality of holes therein, each hole adapted for insertion of a toothbrush therethrough such that the bristle end of the toothbrush rests in the reservoir and the handle end of the toothbrush extends through the hole into the upper chamber, the second plurality of holes being equal to the first plurality of reservoir compartments, the middle divider comprising a set of second track elements adapted for the set of first track elements on the reservoir to slide thereon into and out of a fully engaged position;

a pivotable lid attached to the middle chamber at a hinge and pivotable about the hinge to open and close the upper chamber, the lid further comprising a first snap closure element adapted to interface with a second snap closure element to prevent said lid from moving to an open configuration without user manipulation.

28. The sanitary toothbrush storage unit of claim 27 further comprising:

a quantity of sanitizing liquid in each reservoir compartment, the sanitizing liquid selected from the group consisting of: mouthwash, antiseptic liquid, germicidal liquid, antibacterial liquid, disinfectant liquid, a solution of dilute hypochlorite, a solution of dilute hydrogen peroxide, or a combination thereof.

29. The sanitary toothbrush storage unit of claim 27 further comprising:

a third plurality of toothbrushes each having a bristle end adapted to penetrate said holes in said middle divider, the third plurality of toothbrushes being equal to the first plurality of reservoir compartments and the second plurality of middle divider holes.

* * * * *